Figure 1:
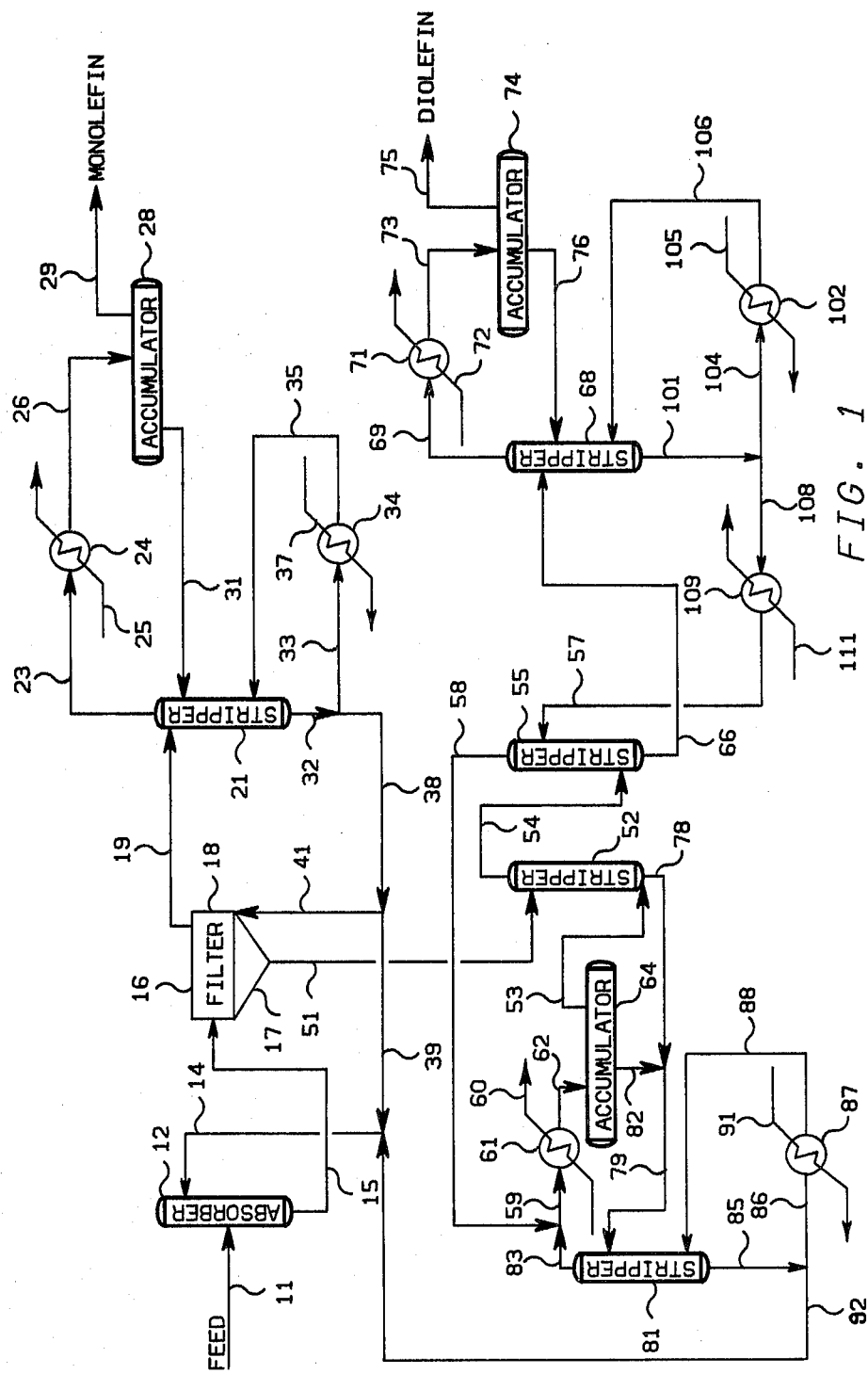

United States Patent [19]

Johnson et al.

[11] 4,400,564

[45] * Aug. 23, 1983

[54] SEPARATION OF MONOOLEFINS FROM DIOLEFINS

[75] Inventors: Marvin M. Johnson; Donald C. Tabler, both of Bartlesville, Okla.

[73] Assignee: Phillips Petroleum Company, Bartlesville, Okla.

[*] Notice: The portion of the term of this patent subsequent to Aug. 9, 2000 has been disclaimed.

[21] Appl. No.: 140,283

[22] Filed: Apr. 14, 1980

[51] Int. Cl.³ .............................................. C07C 7/148
[52] U.S. Cl. ................... 585/845; 260/438.1; 585/844; 585/848
[58] Field of Search ............................... 585/845, 848

[56] References Cited

U.S. PATENT DOCUMENTS

| | | | |
|---|---|---|---|
| 2,381,311 | 8/1945 | Robey et al. | 585/848 |
| 2,386,357 | 10/1945 | Schulze et al. | |
| 2,395,958 | 3/1946 | Soday | 585/845 |
| 2,494,546 | 1/1950 | Fasce | |
| 2,497,159 | 2/1950 | Fasce | 585/848 |
| 3,080,347 | 3/1963 | Sandberg et al. | |
| 3,130,243 | 4/1964 | Dunn et al. | 585/844 |
| 3,517,080 | 6/1970 | Beckham et al. | 585/845 |
| 3,634,530 | 1/1972 | Bills | 585/848 |
| 3,763,200 | 10/1973 | Dines | 585/845 X |
| 4,025,574 | 5/1977 | Tabler et al. | |
| 4,129,605 | 12/1978 | Tabler et al. | |
| 4,141,925 | 2/1979 | Pavlov et al. | 585/848 |

*Primary Examiner*—Helen M. S. Sneed

[57] ABSTRACT

A process and apparatus for separating monoolefins from diolefins comprising contacting a mixture of monoolefins and diolefins with a complexing agent selected from the group consisting of copper(I) salts of sulfonic acids and copper(I) salts of dialkylphosphates and a suitable hydrocarbon solvent for the complexing agent under such conditions that the monoolefins and diolefins form complexes with the complexing agent. The monoolefin complex can be separated from the diolefin complex based either on the relative solubilities of the two complexes in the hydrocarbon solvent for the complexing agent or based on the relative strengths of the two complexes.

19 Claims, 1 Drawing Figure

SEPARATION OF MONOOLEFINS FROM DIOLEFINS

This invention relates to a process and apparatus for separating monoolefins from diolefins.

In chemical processing, the separation of similar compounds has always presented difficulties. Closely similar monoolefins and diolefins may be very difficult to separate. It is thus an object of this invention to provide a process and apparatus for separating monoolefins from diolefins.

In accordance with the present invention, a process and apparatus is provided for the separation of monoolefins from admixture with diolefins by contacting a mixture of monoolefins and diolefins with a complexing agent selected from cuprous salts of sulfonic acids or dialkyl phosphates. The complexing agent is dissolved in a suitable hydrocarbon solvent for the complexing agent to form a complexing reagent. The mixture of monoolefins and diolefins is contacted with the complexing reagent under such conditions that both the monoolefins and diolefins form complexes with the complexing agent. The monoolefin complex can be separated from the diolefin complex based either on the relative solubilities of the two complexes in the complexing reagent solvent or based on the relative strengths of the two complexes.

Generally, there exist a range of temperatures at which the monoolefin complex is soluble in the hydrocarbon solvent for the complexing agent while the diolefin complex is insoluble. At this range of temperatures the monoolefin complex can be separated from the diolefin complex by physical separation processes such as filtering.

The diolefin complex is a stronger complex than the monoolefin complex. Thus, the monoolefin complex can be more readily disassociated in the presence of heat than the diolefin complex. Processes such as distillation can be utilized to separate the monoolefin from the complexing agent while the diolefin remains complexed. The monoolefin can thus be separated from the complexing reagent to effectively separate the monoolefin from the diolefin and recover the monoolefin. The diolefin is subsequently separated from the complexing agent to recover the diolefin.

The use of a suitable hydrocarbon solvent for the complexing agent is a critical feature of the present invention. Water is a common solvent for cuprous salts of sulfonic acids or dialkyl phosphates. However, aqueous solutions of cuprous salts lack stability and are generally unsuitable for forming the complexing reagent. Further, the use of a suitable hydrocarbon solvent for the complexing agent is extremely important from the standpoint of reaction time in forming the monoolefin and diolefin complexes. The monoolefin and diolefins form a single phase with the hydrocarbon solvent and this greatly enhances the reaction time for the formation of the monoolefin and diolefin complexs. In contrast, if water is used as the solvent, the monoolefins and diolefins are immiscible in the water and the complexing agent reacts very slowly with the monoolefins and diolefins.

Other objects and advantages of the invention will be apparent from the foregoing brief description of the invention and the claims as well as from the detailed description of the drawing in which:

FIG. 1 is a diagrammatic illustration of a separation process in accordance with one embodiment of the present invention.

The invention is described in terms of separating normally gaseous monoolefins and diolefins because the invention is particularly applicable to separating normally gaseous monoolefins and diolefins. The invention is also applicable to separating normally liquid monoolefins and diolefins but such a separation will generally require a different apparatus configuration.

Preferably, the separation of the monoolefins from the diolefin is based on the relative solubilities of the monoolefin complex and diolefin complex in the hydrocarbon solvent for the complexing agent. Thus, the process illustrated in FIG. 1 is directed to the separation based on relative solubilities. Example III demonstrates a separation based on the relative strengths of the monoolefin complex and diolefin complex.

The invention is described in terms of a particular apparatus configuration for effecting a separation based on relative solubilities. However, the invention is applicable to any apparatus which provides contact of the mixture of monoolefins and diolefins with the complexing reagent with a subsequent separation and recovery of the monoolefins and diolefins.

Referring now to the drawing, a feed stream containing at least one normally gaseous monoolefin and at least one normally gaseous diolefin is provided through conduit means 11 to the absorption column 12. A complexing reagent which comprises the copper(I) salt complexing agent and a suitable hydrocarbon solvent for the complexing agent is provided through conduit means 14 to the absorber 12. The feed stream flowing through conduit means 11 is contacted with the complexing reagent in the absorption column 12. The absorption column is maintained at a suitable temperature for the monoolefins to form a soluble complex, with the copper(I) salt, in the solvent while the diolefins form an insoluble complex, with the copper(I) salt, in the hydrocarbon solvent.

The reaction mixture containing the soluble monoolefin complex and the insoluble diolefin complex is withdrawn from the absorption column 12 through conduit means 15 and is provided to the filter 16. The insoluble diolefin complex is collected in the lower portion 17 of the filter 16. The soluble monoolefin complex is removed from the upper portion 18 of the filter 16 through conduit means 19 and is provided to the stripping column (referred to hereinafter as a "stripper") 21. Heat is applied to the soluble monoolefin complex in the stripper column 21 to decompose the monoolefin complex. The monoolefin plus some hydrocarbon solvent is removed as an overhead product from the stripper 21 and is supplied through conduit means 23 to the heat exchanger 24. The heat exchanger 24 is provided with a cooling fluid through conduit means 25. The thus cooled overhead stream is provided through conduit means 26 to the overhead accumulator 28. The gaseous monoolefin is removed from the overhead accumulator 28 through conduit means 29. The hydrocarbon solvent is returned from the accumulator 28 to the stripper 21 through conduit means 31. The complexing reagent is removed from the stripper 21 through conduit means 32. At least a portion of the complexing reagent is recycled through conduit means 32, conduit means 33, heat exchanger 34 and conduit means 35 to the stripper 21. A heating fluid is provided to the heat exchanger 34 through conduit means 37. The recycle stream flowing through conduit means 35 is thus utilized to supply heat to the stripper 21. The portion of the complexing reagent flowing through conduit means 32 which is not recycled to the stripper 21 flows through the combination of conduit means 38, 39 and 14 to the absorption column 12. At least a portion of the complexing reagent flowing through conduit means 38 is provided through conduit means 41 to the lower portion 17 of the filter 16. The complexing reagent flowing through conduit means 41 is utilized to reslurry the diolefin complex to provide easy removal of the diolefin complex from the lower portion 17 of the filter 16.

The reslurried diolefin complex is removed from the lower portion 17 of the filter 16 through conduit means 51 and is provided to the stripper 52. Carbon monoxide is provided to the stripper 52 through conduit means 53. Use of carbon monoxide to strip the diolefin from the copper(I) salt is preferred because the diolefin may be stripped by ligand exchange with the carbon monoxide at relatively low temperatures which avoids possible polymerization side reactions which could occur if the diolefin complex were heated. The diolefin and some carbon monoxide are provided from the stripper 52 through conduit means 54 to the stripper 55. An absorption oil is provided to the stripper 55 through conduit means 57. The absorption oil flowing through conduit means 57 is utilized to strip the carbon monoxide from the diolefin. The thus stripped carbon monoxide is removed as an overhead stream from the stripper 55 through conduit means 58 and is provided through the combination of conduit means 59, heat exchanger 61 and conduit means 62 to the overhead accumulator 64. A cooling fluid is provided to the heat exchanger 61 through conduit means 60.

Any suitable absorption oil may be utilized to strip the carbon monoxide from the diolefin. Preferably, the absorption oil utilized is the same as the hydrocarbon solvent utilized in the complexing reagent.

The diolefin and the absorption oil are removed through conduit means 66 from the stripper 55 and are provided to the stripper 68. Heat is utilized to substantially separate the diolefin from the absorption oil. The thus separated diolefin and a small amount of absorption oil is removed as an overhead stream from the stripper 68 through conduit means 69 and is provided to the heat exchanger 71. A cooling fluid is provided to the heat exchanger 71 through conduit means 72. The thus cooled overhead stream is provided from the heat exchanger 71 through conduit means 73 to the overhead accumulator 74. The gaseous diolefin is removed from the accumulator 74 through conduit means 75. The absorption oil in the accumulator 74 is returned to the stripper 68 through conduit means 76.

Absorption oil is removed from the stripper 68 as a bottoms stream through conduit means 101. A portion of the thus removed absorption oil flowing through conduit means 101 is provided to the heat exchanger 102 through conduit means 104. The heat exchanger 102 is provided with a heating fluid through conduit means 105. The thus heated absorption oil is returned from the heat exchanger 102 to the stripper 68 through conduit means 106. The remaining portion of the absorption oil flowing through conduit means 101 is provided through conduit means 108 to the heat exchanger 109. Heat exchanger 109 is provided with a cooling fluid flowing through conduit means 111. The thus cooled absorption oil is provided from the heat exchanger 109 through conduit means 57 to the stripper 55 as has been previously described.

The complexing reagent which is saturated with carbon monoxide is removed as a bottoms stream from the stripper 52 and is provided through the combination of conduit means 78 and 79 to the stripper 81. Hydrocarbon solvent is removed from the accumulator 64 and is provided through the combination of conduit means 82 and 79 to the stripper 81. Heat is utilized to separate the complexing reagent from the carbon monoxide. Carbon monoxide and a small amount of hydrocarbon solvent is removed from the stripper 81 as an overhead product and is provided through the combination of conduit means 83 and 59 to the heat exchanger 61. The complexing reagent is removed as a bottoms stream from the stripper 81 through conduit means 85. A portion of the complexing reagent is recycled to the stripper 81 through the combination of conduit means 86, heat exchanger 87 and conduit means 88. The heat exchanger 87 is provided with a heating fluid through conduit means 91. Thus, heat is supplied to the stripper 81 by the complexing reagent flowing through conduit means 88.

The portion of the complexing reagent flowing through conduit means 85 which is not recycled through the stripper 81 is provided through the combination of conduit means 92 and 14 to the absorber 12.

Any suitable reaction conditions can be utilized in the process of the present invention. In general, the temperature in the absorber 12 will be in the range of about 70° F. to about 120° F. The pressure in the absorber 12 will generally be in the range of about 0 psig to about 10 psig. The temperature in the upper portion 18 of the filter 16 will generally be in the range of about 70° F. to about 120° F. while the pressure will generally be in the range of about 10 psig to about 50 psig. The temperature in the lower portion 17 of the filter 16 will generally be in the range of about 70° F. to about 120° F. while the pressure will generally be in the range of about 0 psig to about 10 psig. The temperature in the stripper 21 will generally be in the range of about 45° F. degrees below the boiling point of the solvent to about the boiling point of the solvent while the pressure will generally be in the range of about 0 psig to about 10 psig. The temperature in the stripper 52 will generally be in the range of about 70° F. to about 120° F. while the pressure will generally be in the range of about 0 psig to about 10 psig. The carbon monoxide flow rate through conduit means 53 will generally be in the range of about 1 gram mole per gram atom of copper to about 2 gram moles per gram atom of copper. The temperature in the stripper 55 will generally be in the range of about 30° F. to about 70° F. while the pressure will generally be in the range of about 20 psig to about 50 psig. The temperature in the stripper 68 will generally be in the range of about 10° F. below the boiling point of the absorption oil to about the boiling point of the absorption oil while the pressure will generally be in the range of about 0 psig to about 10 psig. The temperature in the stripper 81 will generally be in the range of about 10° F. below the boiling point of the solvent to about the boiling point of the solvent while the pressure will generally be in the range of about 0 psig to about 10 psig.

Any suitable monoolefin can be separated from any suitable diolefin in accordance with the present invention. The process of this invention is particularly applicable to separating monoolefins having from 4 to 16 carbon atoms from diolefins having from 4 to 16 carbon atoms. The invention is particularly useful in separating closely similar monoolefins and diolefins. Also, as has been previously stated, the invention is particularly applicable to separating normally gaseous monoolefins and diolefins. Butene may be separated from butadiene, pentene may be separated from pentadiene, hexene may be separated from hexadiene, etc. Further, mixtures of octene, decene, dodecene and the like can be at least partially separated from heptadiene, nonadiene, undecadiene, tridecadiene and the like.

The copper(I) salt complexing agent employed in the present invention is selected from the group consisting of:
  a. the copper(I) salt of an alkane sulfonic acid having from 4 to 20 carbon atoms per molecule;
  b. the copper(I) salt of an aromatic sulfonic acid including hydroxyaromatic and haloaromatic sulfonic acids having from 6 to 22 carbon atoms per molecule;
  c. the copper(I) salt of a petroleum sulfonic acid; and
  d. the copper(I) salt of a dialkyl phosphate having from 1 to 12 carbon atoms per alkyl member.

The presently preferred copper(I) salt is copper(I) dodecylbenzene sulfonate.

The alkane sulfonic acids useful in the practice of this invention can be straight chain or branched. Examples of suitable alkane sulfonic acids include n-butanesulfonic acid, 2-ethyl-1-hexanesulfonic acid, 2-methylnonanesulfonic acid, dodecanesulfonic acid, 2-ethyl-5-n-pentyltridecanesulfonic acid, n-eicosanesulfonic acid, and the like. A presently preferred alkane sulfonic acid is 2-ethyl-1hexanesulfonic acid.

The aromatic sulfonic acids useful in the practice of this invention include benzenesulfonic acid, alkylbenzenesulfonic acids wherein the alkyl member contains from 1 to 16 carbon atoms, such as p-toluenesulfonic acid, p-dodecylbenzenesulfonic acid, p-hexadecylbenzenesulfonic acid, and the like, naphthalenesulfonic acid, phenolsulfonic acid, naphtholsulfonic acids, and halobenzenesulfonic acids, such as p-chlorobenzenesulfonic acid, p-bromobenzenesulfonic acid, and the like. A presently preferred aromatic sulfonic acid is p-dodecylbenzenesulfonic acid. Commercially available mixtures of o-, m-, and p-dodecylbenzenesulfonic acid can be employed. Preferably, the mixture employed is predominantly, i.e., 85–90 mole percent, the para isomer.

The petroleum sulfonic acids useful in the practice of this invention can be prepared from a deasphalted, solvent-refined petroleum fraction having a viscosity of about 140 to about 720 SUS at 210° F. (99° C.). A presently preferred sulfonation stock is a propanefractionated, solvent-extracted, dewaxed Mid-Continent oil of about 200 to 230 SUS at 210° F. (99° C.) and having a viscosity index of about 90 to 100, or higher. A Mid-Continent oil is more precisely defined as a mixed base or intermediate base oil in "The Science of Petroleum", volume 1, page 7, Oxford University Press, London, New York and Toronto, 1938. Such oil is, for example, sulfonated with a 10 weight percent $SO_3$—90 weight percent $SO_2$ mixture in a continuous operation substantially as described in U.S. Pat. No. 3,135,693 to Whitney et al, using an $SO_3$ to oil weight ratio of about 0.08 and a reaction temperature of about 115° F. (46° C.). The total reaction time is about 5 minutes, including the mixing and soaking periods. The system is maintained in the liquid phase at a pressure of 100–120 psig (790–930 kPa). Effluent from the reaction unit is subjected to a two-stage flash for $SO_3$—$SO_2$ removal.

The dialkyl phosphates useful in the practice of this invention include dimethyl phosphate, diethyl phosphate, di-n-butyl phosphate, di-2-ethylhexyl phosphate, di-n-dodecyl phosphate, and the like.

The cuprous salts complexing agent of the present invention is generally prepared by refluxing a solution of the sulfonic acid or dialkyl phosphate in an inert diluent, as hereinafter described, together with cuprous oxide, with provision for removing the water of reaction. The preparation is carried out in an oxygen-free inert atmosphere such as under nitrogen. The preferred molar ratio of acid or dialkyl phosphate to copper is about 1 to 1. The preparation is carried out for a time sufficient to produce substantially complete reaction. The copper(I) salts can, if desired, be separated from the diluent by removing the diluent as by vacuum distillation.

The cuprous salts complexing agent may be utilized in any suitable hydrocarbon solvent. The cuprous salts are normally used at about an 0.5 to 2 molar solution in a hydrocarbon solvent such as paraffinic and aromatic hydrocarbon solvents having from about 5 to about 15 carbon atoms to produce a solution or slurry of the complexing reagent. The choice of solvent is related to the boiling point of the feedstock. The boiling point of the solvent is preferably at least 50–60° F. (28°–33° C.) higher than the boiling point of the feedstock. Examples of suitable aromatic solvents include benzene, the alkyl derivatives of benzene, as for example, toluene, the xylenes, isopropyl benzene, 1,3,5-trimethylbenzene, 1,2,4,5-tetramethylbenzene, hexamethylbenzene, polynuclear aromatic hydrocarbons such as naphthalene, anthracene, and the like. Examples of suitable paraffinic solvents include n-hexane, n-octane, n-decane and the like. The solvent used in forming the cuprous salt complexing reagent for separation of normally liquid olefins is dictated by the boiling point of the olefin or the feedstock containing it. Para-xylene can also be employed as the solvent for the reagent when $C_5$–$C_7$ monoolefins are to be separated from diolefins. The aromatic solvents are more preferred than the paraffinic solvents because a solution of the copper(I) salt and an aromatic solvent is more stable than (a solution of the copper (I) salt and a paraffinic solvent.

It is desirable to have as much of the copper(I) salt in the complexing reagent as possible. The higher the salt/solvent ratio, the greater will be the complexing capacity of the system, and the greater the amount of unsaturated hydrocarbon that can be complexed. Salt/solvent molarities of at least 0.5 mole of salt per liter of solvent have given highly satisfactory results. However, at a molarity of about 2 or more, the solution viscosity can increase enough to cause pumping difficulties, and such viscous solutions are preferably avoided.

The advantages of employing the cuprous salts of this invention over other cuprous compounds such as cuprous halides are numerous. These include low corrosivity of process equipment, particularly those fabricated from stainless steel, and water tolerance. In addition, the cuprous salts of this invention, depending upon the nature of the hydrocarbon portion of the molecule, are soluble in both aromatic and paraffinic hydrocarbon solvents whereas the cuprous halides are soluble in aromatic hydrocarbons by virtue of forming weak pi-complexes with the aromatic, hence it is not expected to be soluble in aliphatic hydrocarbons. The presently preferred cuprous salt of this invention, i.e., copper(I)

dodecylbenzene sulfonate, also forms a weak pi-complex, but this is apparently not the only mechanism of solubility because the cuprous sulfonate is also soluble in aliphatic hydrocarbons.

The following examples are presented in further illustration of the invention.

EXAMPLE I

Copper(I) sulfonate complexing reagent was prepared by reacting 14.2 g (0.10 mole) of cuprous oxide with 66.0 g (0.20 mole) of Richonic acid B (a purified n-dodecylbenzenesulfonic acid obtained from The Richardson Co., Des Plaines, IL) dissolved in m-xylene. The resulting mixture was heated to reflux under a nitrogen blanket. Water that formed from the reaction was collected in a Dean-Stark trap. During 45 minutes of refluxing 0.14 mole of water was collected. The concentration of the copper (I) sulfonate in the resulting solution was determined to be 0.84 molar by the capacity of the resulting solution to absorb carbon monoxide.

A portion of the thus prepared copper(I)sulfonate complexing reagent was placed in an absorption flask that was part of a vacuum line. After removal of air by evacuation, increments of 1,3-butadiene gas were added to the flask while the complexing agent was being stirred with a magnetic stirrer. The complexing reagent in the absorption flask was maintained at about 25° C. Essentially complete absorption of the butadiene in the complexing reagent was observed. The absorption of the butadiene was accompanied by the formation of a pea green, waxy solid on the wall of the flask illustrating that a solid state reaction product is formed by the reaction of the copper(I) sulfonate and the diolefin (butadiene).

EXAMPLE II

A copper(I) sulfonate complexing reagent having a 1.078 molar concentration of copper(I) sulfonate was prepared in the same manner as described in Example I. A 20 ml portion of the thus prepared copper(I) sulfonate complexing reagent was placed in a Diels-Alder tube. The Diels-Alder tube was filled with nitrogen and maintained at about 25° C. Next, 2.1 ml (0.0212 moles) of 2-methyl-1,3-butadiene (isoprene) was added to the copper(I) sulfonate complexing reagent in the Diels-Alder tube. A crystalline solid resulted from the reaction of the copper(I) sulfonate and the isoprene which again indicates that a solid state reaction product is formed by the reaction of the copper(I) sulfonate and the diolefin (isoprene).

EXAMPLE III

Separation of a monoolefin from a diolefin on the basis of the relative volatility of their complexes was demonstrated in a run in which 200 ml of the copper(I) sulfonate complexing reagent from Example I, together with 7.0 g each of 2-methylbutene-2 and isoprene were placed in a distilling flask. The mixture in the distilling flask was distilled through an efficient packed column 1.5 cm. i.d. × 30 cm. The resulting distillate was sequentially collected in five approximately 10-ml fractions. The boiling range of these five collected fractions and their composition as determined by gas-liquid chromatography are shown in Table I.

TABLE I

| Fraction | Boiling Point, °C. | | GLC Analysis, Area % | | | |
|---|---|---|---|---|---|---|
| | Start | Finish | 2-MB-2 | Isoprene | Toluene | Xylenes |
| 1 | 36.0 | 135.5 | 76.82 | 14.73 | 1.09 | 7.36 |
| 2 | 133.3 | 137.0 | 9.37 | 4.70 | 0.63 | 85.29 |
| 3 | 137.0 | 138.0 | 0.61 | 0.94 | trace | 98.46 |
| 4 | 136.0 | 137.0 | 1.71 | 1.13 | 0 | 97.16 |
| 5 | 137.0 | 138.0 | 0.24 | 0.22 | 0 | 99.53 |

The data set forth in Table I illustrate that a much larger fraction of the insoluble diolefin complex remains in the solution than of the soluble monoolefin complex. After distilling until the distillate contained over 99.5 percent xylenes, 6.06 grams of 2-methylbutene-2 had been recovered while only 1.56 grams of isoprene had been recovered. This indicates that only 22.2 percent of the isoprene had escaped from the solution versus 86.6 percent of the 2-methylbutene-2.

Reasonable variations and modifications are possible within the scope of the disclosure and the appended claims to the invention.

That which is claimed is:

1. A process for at least partially separating at least one monoolefin from admixture with at least one diolefin comprising the steps of:
   contacting the mixture of at least one monoolefin and at least one diolefin with a complexing agent selected from the group consisting of copper(I) salts of sulfonic acids and copper(I) salts of dialkyl phosphates and a suitable hydrocarbon solvent for said complexing agent under such conditions that the at least one monoolefin forms a substantially soluble complex, in said suitable hydrocarbon solvent, with said complexing agent and the at least one diolefin forms a substantially insoluble complex, in said suitable hydrocarbon solvent, with said complexing agent; and
   separating said substantially insoluble complex from the solution of said suitable hydrocarbon solvent which contains said substantially soluble complex to thereby effectively separate said at least one monoolefin from said at least one diolefin.

2. A process in accordance with claim 1 additionally comprising the steps of:
   separating said at least one diolefin in said substantially insoluble complex from said complexing agent; and p1 separating said at least one monoolefin in said substantially soluble complex from the solution of said suitable hydrocarbon solvent which contains said substantially soluble complex.

3. A process in accordance with claim 1 wherein said complexing agent is selected from the group consisting of:
   (a) the copper(I) salt of an alkane sulfonic acid having from 4 to 20 carbon atoms per molecule;
   (b) the copper(I) salt of an aromatic sulfonic acid having from 6 to 22 carbon atoms per molecule including hydroxyaromatic and haloaromatic sulfonic acids;
   (c) the copper (I) salt of a petroleum sulfonic acid; and
   (d) the copper(I) salt of a dialkyl phosphate having from 1 to 12 carbon atoms per alkyl member.

4. A process in accordance with claim 1 wherein said complexing agent is copper(I) dodecylbenzene sulfonate.

5. A process in accordance with claim 2 wherein said at least one diolefin is separated from said complexing agent by contacting the substantially insoluble complex containing said at least one diolefin with carbon monoxide.

6. A process in accordance with claim 2 wherein said at least one monoolefin is separated from the solution of said suitable hydrocarbon solvent which contains said substantially soluble complex by subjecting the solution of said suitable hydrocarbon solvent which contains said substantially soluble complex to heat.

7. A process in accordance with claim 1 wherein said at least one monoolefin is a monoolefin having from 4 to 16 carbon atoms and said at least one diolefin is a diolefin having from 4 to 16 carbon atoms.

8. A process in accordance with claim 7 wherein said at least one monoolefin is a normally gaseous monoolefin and said at least one diolefin is a normally gaseous diolefin.

9. A process in accordance with claim 1 wherein said suitable hydrocarbon solvent is a paraffinic or aromatic hydrocarbon solvent having from 6 to 15 carbon atoms.

10. A process in accordance with claim 1 wherein said suitable hydrocarbons solvent is m-xylene.

11. A process in accordance with claim 1 wherein said substantially insoluble complex is separated from the solution of said suitable hydrocarbon solvent which contains said substantially soluble complex by filtration.

12. A process for at least partially separating at least one monoolefin from admixture with at least one diolefin comprising the steps of:

contacting the mixture of at least one monoolefin and at least one diolefin with a complexing agent selected from the group consisting of copper(I) salts of sulfonic acids and copper(I) salts of sulfonic acids and copper(I) salts of dialkylphosphates and a suitable hydrocarbon solvent for said complexing agent, wherein the complex formed between said at least one diolefin and said complexing agent is stronger than the complex formed between said at least one monoolefin and said complexing agent;

heating the solution containing the complex of said at least one monoolefin and said complexing agent and the complex of said at least one diolefin and said complexing agent to thereby separate said at least one monoolefin from said complexing agent and said solution to thereby effectively separate said at least one monoolefin from said at least one diolefin.

13. A process in accordance with claim 12 additionally comprising the step of separating said at least one diolefin from said complexing agent and said suitable hydrocarbon solvent for said complexing agent.

14. A process in accordance with claim 12 wherein said complexing agent is selected from the group consisting of:
(a) the copper(I) salt of an alkane sulfonic acid having from 4 to 20 carbon atoms per molecule;
(b) the copper(I) salt of an aromatic sulfonic acid having from 6 to 22 carbon atoms per molecule including hydroxyaromatic and haloaromatic sulfonic acids;
(c) the copper (I) salt of a petroleum sulfonic acid; and
(d) the copper(I) salt of a dialkyl phosphate having from 1 to 12 carbon atoms per alkyl member.

15. A process in accordance with claim 12 wherein said complexing agent is copper(I) dodecylbenzene sulfonate.

16. A process in accordance with claim 12 wherein said at least one monoolefin is a monoolefin having from 4 to 16 carbon atoms and said at least one diolefin is a diolefin having from 4 to 16 carbon atoms.

17. A process in accordance with claim 16 wherein said at least one monoolefin is a normally gaseous monoolefin and said at least one diolefin is a normally gaseous diolefin.

18. A process in accordance with claim 12 wherein said suitable hydrocarbon solvent is a paraffinic or aromatic hydrocarbon solvent having from 6 to 15 carbon atoms.

19. A process in accordance with claim 12 wherein said suitable hydrocarbon solvent is m-xylene.

* * * * *